(12) United States Patent
Tan

(10) Patent No.: US 7,195,615 B2
(45) Date of Patent: Mar. 27, 2007

(54) SYSTEM FOR PROVIDING A MEDICAL DEVICE WITH ANTI-MICROBIAL PROPERTIES

(75) Inventor: Sharon Mi Lyn Tan, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/438,063

(22) Filed: May 14, 2003

(65) Prior Publication Data

US 2004/0230162 A1   Nov. 18, 2004

(51) Int. Cl.
*A61M 5/00*  (2006.01)

(52) U.S. Cl. ...................... 604/171; 604/265

(58) Field of Classification Search ............... 604/192, 604/110, 263, 198, 187, 158, 164, 160–163, 604/171–172, 197, 256, 93.01, 199, 167.06, 604/523, 533, 905, 513, 265; 128/919, 912, 128/DIG. 26
See application file for complete search history.

(56) References Cited

U.S. PATENT DOCUMENTS

| | | | | |
|---|---|---|---|---|
| 3,894,540 A | * | 7/1975 | Bonner, Jr. .................. 604/171 |
| 4,412,834 A | * | 11/1983 | Kulin et al. ................... 604/29 |
| 4,432,764 A | * | 2/1984 | Lopez .......................... 604/533 |
| 4,457,749 A | * | 7/1984 | Bellotti et al. ................. 604/29 |
| 4,998,713 A | * | 3/1991 | Vaillancourt ................ 604/537 |
| 5,004,455 A | | 4/1991 | Greenwood et al. |
| 5,059,186 A | | 10/1991 | Yamamoto et al. |
| 5,122,123 A | * | 6/1992 | Vaillancourt ................ 604/192 |
| 5,163,908 A | * | 11/1992 | Lambert ...................... 604/110 |
| 5,236,703 A | * | 8/1993 | Usala ........................ 424/78.36 |
| 5,242,398 A | * | 9/1993 | Knoll et al. ............ 604/103.05 |
| 5,269,755 A | | 12/1993 | Bodicky |
| 5,312,366 A | * | 5/1994 | Vailancourt .................. 604/192 |
| 5,354,267 A | * | 10/1994 | Niermann et al. ............. 604/32 |
| 5,411,550 A | | 5/1995 | Herweck et al. |
| 5,437,656 A | * | 8/1995 | Shikani et al. ........... 604/891.1 |
| 5,487,728 A | * | 1/1996 | Vaillancourt .................. 604/86 |
| 5,536,258 A | * | 7/1996 | Folden ......................... 604/265 |
| 5,567,495 A | | 10/1996 | Modak et al. |
| 5,958,440 A | * | 9/1999 | Burrell et al. ............... 424/409 |
| 6,238,371 B1 | | 5/2001 | Himbert et al. ............. 604/187 |
| 6,280,423 B1 | | 8/2001 | Davey et al. |

(Continued)

FOREIGN PATENT DOCUMENTS

GB   1240312   7/1971

(Continued)

*Primary Examiner*—Nicholas D Lucchesi
*Assistant Examiner*—Christopher D. Koharski
(74) *Attorney, Agent, or Firm*—Mayer & Williams PC; Keum J. Park, Esq.

(57) ABSTRACT

A system for providing medical device with anti-microbial properties to prevent infections. The system includes a medical device having a portion for insertion into the body of a patient, a lumen, and a substrate comprising an anti-microbial agent to be inserted into the lumen of the medical device. To protect the substrate from anti-microbial agents during insertion into the lumen, the system further includes a collapsible cover connected to the substrate. A connector can be used for attaching the substrate to the cover. The substrate may be an iodine-based rod. A guidewire may be attached to the connector to further facilitate insertion of the substrate into the lumen.

17 Claims, 3 Drawing Sheets

U.S. PATENT DOCUMENTS

| | | |
|---|---|---|
| 6,319,226 B1 | 11/2001 | Sherry |
| 6,602,241 B2 * | 8/2003 | Makower et al. ............ 604/509 |
| 6,939,569 B1 * | 9/2005 | Green et al. ................ 424/667 |
| 2002/0078963 A1 * | 6/2002 | Rouns et al. ........... 128/207.16 |
| 2003/0175323 A1 * | 9/2003 | Utterberg et al. ............ 424/423 |
| 2004/0092890 A1 * | 5/2004 | Ash ........................... 604/264 |
| 2004/0210208 A1 * | 10/2004 | Paul et al. .................. 604/500 |

FOREIGN PATENT DOCUMENTS

| | | |
|---|---|---|
| WO | WO 99/52509 A | 10/1999 |
| WO | WO 00/74743 | 12/2000 |

* cited by examiner

SYSTEM FOR PROVIDING A MEDICAL DEVICE WITH ANTI-MICROBIAL PROPERTIES

FIELD OF THE INVENTION

The invention generally relates to medical devices that are inserted into the body of a patient. More particularly, the invention is directed to a system for providing medical devices with anti-microbial properties and methods for making such a system and medical devices having anti-microbial properties.

BACKGROUND OF THE INVENTION

Implanted medical devices such as venous and arterial catheters, neurological prostheses, wound drains, urinary "Foley" catheters, peritoneal catheters, and other lumenal in-dwelling devices, have been useful for treating various medical conditions. However, a drawback to implanted medical devices is the risk of infection while the medical device is inserted in the body, and thereafter. Such risk exists even though the medical devices are sterilized and carefully packaged to guard against introduction of microbes or pathogens during implantation or insertion of the medical device. For example, there is a risk of serious nosocomial infections when using catheters for hemodialysis procedures. In fact, central venous catheters account for most nosocomial catheter-related bloodstream infections.

When catheters and other in-dwelling luminal devices are inserted into body cavities such as the urinary tract, venous or arterial vessels, bacteria or other microbes can be picked up from the skin or the catheter hub, lumen or infusate and transfered onto the insertion site where bacterial or microbial colonization may ensue. Once the microorganisms adhere to the catheter surface, it colonizes the surface. These bacteria enhance their adherence rapidly by producing an extracellular slime that makes up the microbial substance of the biofilm. The biofilm layer made of microbial and host substances acts as a protective barrier.

In the case of urinary and venous catheters, there is a significant threat of microbial growth along the exterior surface or outer wall of the catheter and, especially for catheters used long-term, there is a significant threat of microbial grown along the interior surface or inner wall. This can lead to chronic urinary tract infections (CUTI), or septicemia in the case of venous and arterial catheters, thrombolytic emboli, stenosis, and thrombosis resulting from infections, and other life threatening complications, especially among the elderly and immuno-compromised patients. Thus, there is a need for the development of better methods of preventing and treating infections caused by the insertion of catheters into body cavities.

There have been many attempts to prevent such infections. For example, central venous catheters have been developed with chlorohexidine and silver sulfadiazine coatings (ArrowG+ard) and with a combination of minocycline and rifampin coatings (see, e.g., Cook Spectrum™). However, these antiseptic/antibiotic-impregnated catheters have not been adequate, as they have only been shown to reduce the incidence of catheter related infections in the short term, such as less than 30 days. Thus, there is a need for improved catheters that are effective in reducing infections in the long-term.

Iodine-based interventional devices have also been used to minimize the risk of nosocomial bloodstream infection. In particular, an iodine-based, soft, flexible poly-carbonate fiber in the shape of a rod has been placed inside of in-dwelling catheters, as discussed in WO 00/74743 A1. Generally, these polymeric-matrices are chemically and geometrically configured to enable a controlled-release of monomeric iodine at specific conditions such as temperature, making them extremely useful as anti-infective substrates for the effective management of catheter-based nosocomial blood stream infections. Since the surface of the catheter polymer is semi-permeable, the iodine egresses to the exterior surface of the in-dwelling catheter.

Such iodine-loaded rod is inserted into a catheter by gently sliding the rod into the inlet and outlet ports of a lumen of the catheter while holding the rod between the thumb and index fingers. Due to the flexibility of the rod, resistance may be encountered while gently threading it into the lumen. Inserting this rod into the catheter, without contamination, is an arduous and challenging exercise. Even with the use of gloves, there is a potential for contamination. Thus, it is desirable for the rod to remain sterile and, therefore, out of direct contact with equipment, hands, and any other non-sterile surfaces during insertion of the iodine-based rod into the catheter.

Accordingly, there is a need for a medical device that can prevent or reduce the incidences of infection, such as nosocomial infection, during use of medical devices.

Thus, there is a need for an implanted medical device that can more effectively provide anti-infective activity. In particular, there is a need for a medical device that includes a substrate containing an anti-microbial agent that can be inserted into a medical device with a reduced risk of infection at the site of the implanted medical device. There is also a need for a medical device that can provide long-term anti-microbial or anti-infection activity.

There is a further need for an improved method of making such a medical device having anti-infective activity. There is also a need for a method in which an anti-infective substrate is inserted into a medical device such as a catheter in a manner that maintains the sterility and strength of the substrate during insertion.

SUMMARY OF THE INVENTION

These and other objectives are accomplished by the present invention. In one embodiment, the present invention is a system for providing a medical device with anti-microbial properties. The system comprises a medical device, having a portion for insertion into the body of a patient, wherein the medical device comprises a lumen having a distal portion and a proximal portion. The system also includes a substrate comprising an anti-microbial agent, wherein the substrate has a first end and a second end. The substrate is capable of being inserted into the lumen in a manner such that the first end of the substrate is closer to the distal portion of the lumen than the second end of the substrate. The system further comprises a collapsible cover for protecting the substrate during insertion of the substrate into the lumen. The cover is connected to the substrate. Preferably, a connector is attached to an end of the substrate for connecting the substrate to the cover. The system may further comprise a guidewire attached to the connector and in contact with the substrate to aid in the insertion of the substrate into the lumen.

Another embodiment of the present invention is directed to a system for providing a catheter with anti-microbial properties. In this embodiment, the system comprises a catheter for insertion into the body of a patient having a lumen that has a proximal portion and a distal portion; and a rod comprising an iodine-based substance, wherein the rod has a first end and second end. The rod is capable of being inserted into the lumen in a manner such that the first end of the substrate is closer to the distal portion of the lumen than the second end of the substrate. The system further comprises a collapsible cover for protecting the rod during insertion of the rod into the lumen; and a cap attached to the second end of the rod for connecting the rod to the cover. This system may further comprise a guidewire attached to the cap to facilitate insertion of the rod into the lumen. The present invention also provides for a catheter having anti-microbial properties provided by this system.

In yet another embodiment, a method for assembling a medical device, having anti-microbial properties is provided. This method comprises obtaining a medical device having a lumen therein, wherein the lumen has a distal portion and a proximal portion, and obtaining a substrate comprising an anti-microbial agent. The substrate has a first end and a second end and is capable of being inserted into the lumen. The method further comprises connecting the substrate to a collapsible cover for protecting the substrate during insertion of the substrate into the lumen; and inserting the substrate into the lumen. The substrate is inserted into the lumen in a manner such that the first end of the substrate is closer to the distal portion of the lumen than the second end of the substrate. The substrate may be connected to the substrate with a connector, such as a cap. This method may further comprise attaching a guidewire to the connector, wherein the guidewire contacts the substrate to facilitate insertion of the substrate into the lumen. In addition, the method may further comprise filling the lumen with an aqueous solution prior to inserting the substrate into the lumen.

Accordingly, the present invention provides a system that can prevent or reduce the incidences of infection, such as nosocomial infection, during use of medical devices. The present invention also provides for method of assembling a medical device that can more effectively provide anti-microbial activity and reduce the risk of infection.

BRIEF DESCRIPTION OF THE FIGURES

FIG. 1A also shows the substrate comprising an anti-microbial agent to be used in connection with the medical device system of the present invention. In this embodiment, the substrate is in the form of an elongated rod, wherein the rod is attached to the cap. The collapsible cover is in the form of a tube that surrounds the rod. The rod has not been inserted into a lumen of the medical device and the cover is not in a collapsed position.

FIG. 2 shows the cover (also shown in FIGS. 1 and 1A) collapsing as the rod is inserted into the lumen at the proximal end of the catheter. Though in a collapsed position, the cover still surrounds the portion of the rod that has not been inserted into the lumen in order to prevent contamination and introduction of microbes into the catheter.

FIG. 4 also shows a part of a rod that has been inserted into the catheter and has been inserted into the one-way valve.

DESCRIPTION OF THE PREFERRED EMBODIMENTS

Figure 1:
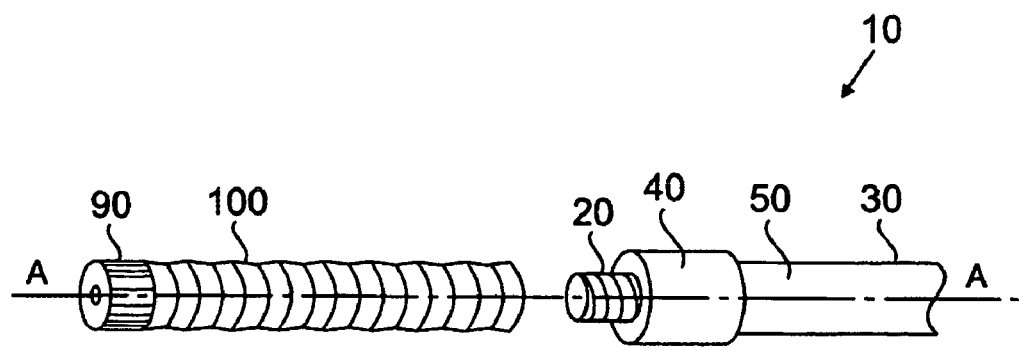
FIG. 1 shows a cap, a collapsible cover that is attached to the cap, and a catheter to be used in connection with a system of the present invention. The collapsible cover protects a substrate (not shown) that is to be inserted into the lumen of the catheter.
Figure 1A:
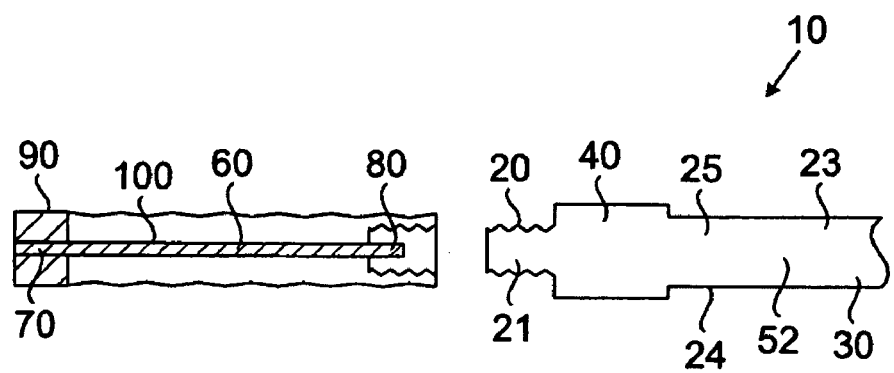
FIG. 1A is a cross-sectional view of the cap, cover, and catheter of FIG. 1. along the longitudinal axis marked A—A.

In one embodiment of the medical device system of the present invention, the medical device is a catheter 10 having a proximal portion 20 and a distal portion 30 as shown in FIG. 1. The catheter 10 generally comprises an elongated shaft which extends along a longitudinal axis between the proximal portion 20 and the distal portion 30. FIG. 1 A shows a cross-sectional view along the longitudinal axis of the catheter 10 in FIG. 1. As shown in FIG. 1A, the outer wall 24 of the catheter 10 surrounds an interior passageway, or a lumen 25 which extends along the longitudinal axis from the proximal portion 20. The lumen 25 has a proximal portion 21 and a distal portion 23. The proximal portion 20 of the catheter 10 preferably includes a hub 40 and the distal portion 30 may include an extension tube 50. This extension tube 50 may be an inlet lumen 52. The catheter 10 of the present invention may have more than one lumen. For example, the catheter 10 may further include an outlet lumen. Also, the catheter 10 can include a lumen for blood perfusion.

Any catheter 10 used for medical treatment can generally be used for the present invention. Suitable catheters include, but are not limited to, venous, arterial, urinary, and percutaneous catheters, sheaths and trocars, drainage catheters, endoscopes and endoscopic catheters, and gastrointestinal catheters. In addition to catheters, other medical devices that have at least one lumen and are insertable into the body of a patient and accessible through the skin or other method once implanted can be used in the present invention. For example, the following other luminal in-dwelling medical devices may be used: cannulas, cardiac pacemaker leads or lead tips, cardiac defibrillator leads or lead tips, implantable vascular access ports, blood tubing, vascular or other grafts, intra-aortic balloon pumps, heart valves, cardiovascular sutures, total artificial hearts and ventricular assist pumps.

Suitable medical devices may be made of any suitable material as known to one skilled in the art. For example, the medical devices suitable for the present invention may be fabricated from polymeric materials. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Preferably, the medical device is made from a polymer, such as polyethylene, polyurethane, polycarbonate, silicone, ethyl vinyl acetate, polypropylene, polyamides, polyimides, PEBAX or similar material. The medical device may be made by any method known to one skilled in the art.

The medical device system of the present invention also includes a substrate 60 comprising an anti-microbial agent that is inserted into a lumen of a medical device. As shown in FIG. 1A, the substrate 60 has a first end 80 and a second end 70. Preferably, the substrate 60 is in the shape of a rod or tube so that it can easily be inserted into the lumen 25 of the medical device or catheter 10. The substrate 60 is inserted into the lumen 25 of the medical device such that the first end 80 is positioned closer to the distal portion 23 of the lumen 25 than the second end 70.

The substrate 60 comprises an anti-microbial agent for preventing infection. Suitable anti-microbial agents include, but are not limited to, elemental iodine (also called free iodine), hypohalites, haloamines, thiocyanogen, hypothiocyanite, silver ions, triclosan, antibiotics such as penicillin and amoxycillan, and rapromycin. Preferably, the anti-microbial agent is an iodine-based substance.

The substrate 60 can be formed from the anti-microbial agent. For example, the substrate 60 may be made of an iodine-polycarbonate material. Alternatively, the substrate 60 can be formed from a material that does not contain an anti-microbial agent. For example, the material may be a polymer that is biodegradable or non-biodegradable. In addition, the polymer that may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example.

Preferred materials include, but are not limited to, polyurethane, polycarbonate, silicone, ethyl vinyl acetate, polypropylene, polyamides, polyimides, PEBAX or similar material. The material may be biodegradable or non-biodegradable.

The amount of the anti-microbial agent can be varied according to the desired effect. Also, different amounts of anti-microbial agent can be present along the length of the substrate 60. For example, the concentration of the anti-microbial agent at one end of the substrate 60 can be greater than the concentration of the anti-microbial agent at the other end of the substrate 60. However, a uniform amount of the anti-microbial agent along the substrate 100 is preferred. The manufacture of the substrate 60 and the use of the substrate 60 for providing anti-microbial activity is described in WO 00/74743 A1.

To protect the substrate 60 during insertion of the substrate 60 into the lumen 25 of the catheter 10, a connector such as a cap 90 can be attached to the second end 70 of the substrate 60, as shown in FIG. 1A. The substrate 60 may be inserted into the lumen 25 by handling the cap 90 instead of the substrate 60 itself in order to avoid contamination and reduce the risk of introducing infection into the catheter 10. The cap 90 may be removably attached to the substrate 60 so that after the substrate 60 is inserted, the cap 90 may be detached from the substrate 60. The connector or cap 90 may be made of any suitable materials as known to one skilled in the art.

To further protect the substrate 60 during insertion of the substrate 60 into the lumen 25 of the medical device, a collapsible cover 100 is attached to the cap 90 as shown in FIGS. 1 and 1A. The cover 100 is preferably tubular in shape and surrounds at least a portion of the substrate 60. Preferably, the cover 100 substantially surrounds the substrate 60 before the substrate 60 is inserted into the lumen 25 and also extends at least the length of the substrate 60 as shown in FIGS. 1 and 1A. The cover 100 collapses as the substrate 60 is inserted into the lumen 25 as shown in FIG. 2.

Figure 2:
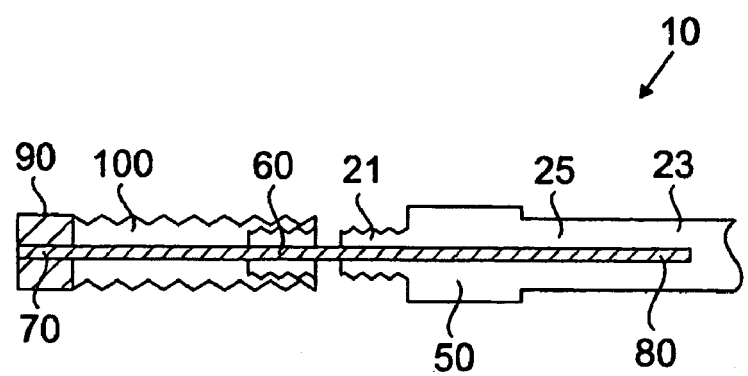
FIG. 2 shows a cross-sectional view of an embodiment of the present invention in which the substrate comprising an anti-microbial agent of FIG. 1A is partially inserted into the lumen of a catheter. The catheter is shown in a cross-sectional view along line A—A of FIG. 1.

FIG. 2 shows an embodiment of the present invention in which the substrate 60 of FIG. 1 is partially inserted into the lumen 25. (The catheter 10 is shown in a cross-sectional view along its longitudinal axis.) FIG. 2 shows a view of the cover 100 (also shown in FIGS. 1 and 1A) collapsing as the substrate 60 is inserted into the proximal portion 21 of the lumen 25. Though in a collapsed position, the cover 100 still surrounds the portion of the substrate 60 that has not been inserted into the lumen 25 in order to prevent contamination and the introduction of infection into the catheter 10. Thus, as the substrate 60 is being inserted, the cover 100 collapses but still protects the portion of the substrate 60 that has not yet been inserted into the lumen 25.

It is preferred that the cover 100 is manufactured from a material that can prevent the migration of iodine or other anti-microbial agents from the substrate 60 before the substrate 60 is placed in the lumen 25. Suitable materials include without limitation polyurethane and its copolymers, silicone and its copolymers, ethylene vinyl-acetate, polyethylene terephthalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins. Preferred materials include, but are not limited to, polyethylene terephthalate, polypropylene, polystyrene, polyethylene, and polyurethane.

Figure 3:
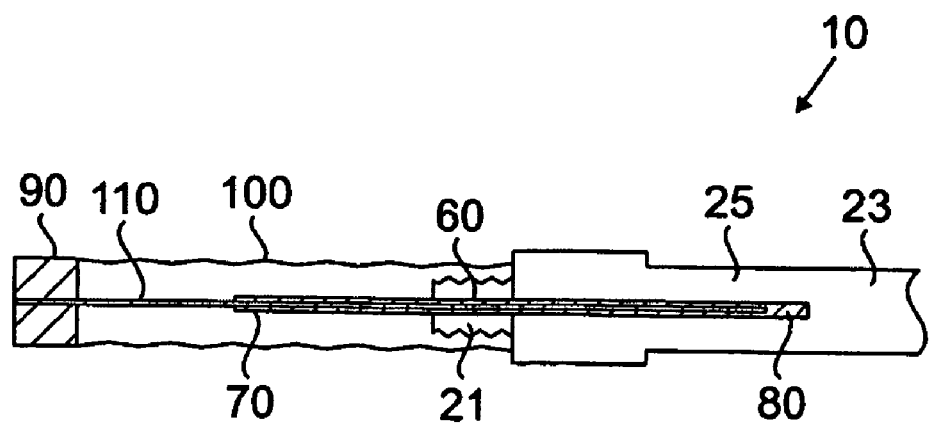
FIG. 3 depicts a cross-sectional view of another configuration of the cap and substrate to be used in connection with a further embodiment of a medical device system of the present invention. The catheter is shown in a cross-sectional view along line A—A of FIG. 1. In this embodiment, the cap has a guidewire attached thereto and extending perpendicularly from the cap. The guidewire is disposed in a cavity within the rod along the longitudinal axis of the rod. The guidewire provides strength to the rod during insertion.

A guidewire 110 may also be attached to the connector or cap 90 and placed in contact with the substrate 60 to facilitate the insertion of the substrate 60 into the lumen 25. The guidewire 110 may be manufactured out of any suitable materials as known by one skilled in the art. FIG. 3 shows an embodiment of the present invention in which a guidewire 110 is attached to the cap 90. In this embodiment, the guidewire 110 extends generally perpendicularly from the cap 90.

The guidewire 110 facilitates insertion of the substrate 60, which may be very flexible and difficult to maneuver, into the lumen 25 without breaking the substrate 60. The guidewire 110 provides strength to the substrate 60 and prevents it from breaking. When a guidewire 110 is used to insert the substrate 60, the substrate 60 preferably has a hollow cavity along its longitudinal axis. The guidewire 110 is inserted into this cavity in order to facilitate insertion of the rod and provide strength to the rod during insertion. The substrate 60 may also be formed around a guidewire 110. The cap 90 and the guidewire 110 may be removed after the substrate 60 has been placed in the lumen 25.

To prevent backflow of bodily fluids through the lumen 25 during the insertion of the substrate 60, a one-way valve 120 may be placed in the lumen 25 at its distal portion 23. The one-way valve 120 also assists in guiding the substrate 60 during insertion. The one-way valve 120 is preferably placed closer to the distal portion 23 of the lumen 25 than the proximal portion 21 of the lumen 25 such that at least a portion of the first end 80 of the substrate 60 passes through the valve 120 as the substrate 60 is inserted and positioned in the lumen 25. Using a one-way valve 120 instead of a clamp is advantageous because the clamp prevents backflow when removing and/or inserting the rod. When the cap 90 is removed and the clamp is open, there is a chance of backflow of blood.

Figure 4:
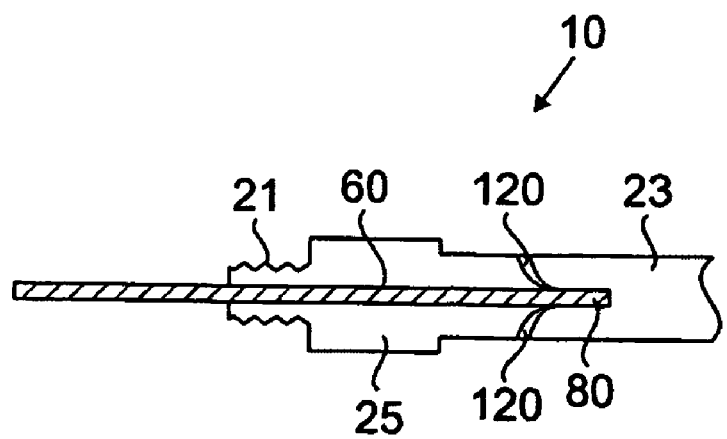
FIG. 4 depicts a catheter to be used in connection with the medical device system of the present invention. A cross-sectional view of the catheter along its longitudinal axis is shown. The catheter includes a hub at its proximal portion and an extension hub at its distal portion. The catheter has a one-way valve at its distal portion.

FIG. 4 depicts a catheter 10 having a one-way valve 120 in its lumen 25. The catheter 10 includes a hub 40 at its proximal portion 20 and an extension tube 50 at its distal portion 30. The catheter 10 has a one-way valve 120 located at the distal portion 23 of the lumen 25. FIG. 4 also shows a substrate 60 that has been inserted into the lumen 25 and has been inserted into the one-way valve 120.

Figure 5:
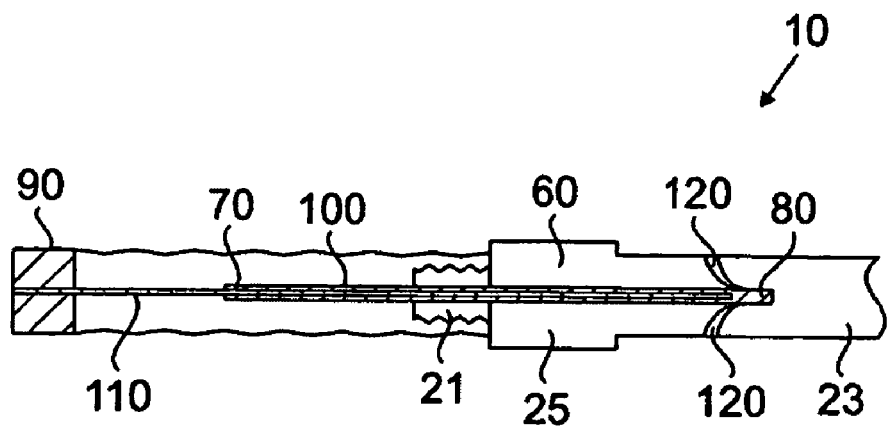
FIG. 5 shows a cross-sectional view of a configuration of the present invention wherein the cap includes a guidewire as shown in FIG. 3 and the substrate or rod is being inserted into a catheter having a one-way valve, as shown in FIG. 4. The guidewire guides the rod into the catheter and through the one-way valve.

FIG. 5 shows a configuration of the present invention wherein the cap 90 includes a guidewire 110 as shown in FIG. 3 and the substrate 60 is being inserted into a catheter 10 having a one-way valve 120, as shown in FIG. 4. The guidewire 110 guides the rod or substrate 60 into the lumen 25 and through the one-way valve 120. As shown in FIG. 5, the guidewire 110 can also be molded into a tube, wherein the ends of the tube are sealed.

An aqueous solution may also be contained in the lumen 25 of the catheter 10 or medical device. The aqueous solution may be any solution that can serve as a release medium for the anti-microbial agent. Suitable solutions include, but are not limited to, saline, heparin, and sterile water. Once the substrate 60 is positioned in the lumen 25, the substrate 60 is exposed to the aqueous solution. The aqueous solution allows the anti-microbial agent, such as iodine, to migrate from the substrate 60 and enter the liquid phase. By egressing from the substrate 60 and entering the liquid phase in the aqueous solution, the iodine or anti-microbial agent can proliferate along the entire length of the lumen 25 to provide anti-infection activity. The lumen 25 does not have to contain an aqueous solution, in which case the anti-microbial agent would egress from the substrate 60 and enter the gaseous phase in the lumen 25.

Figure 6:
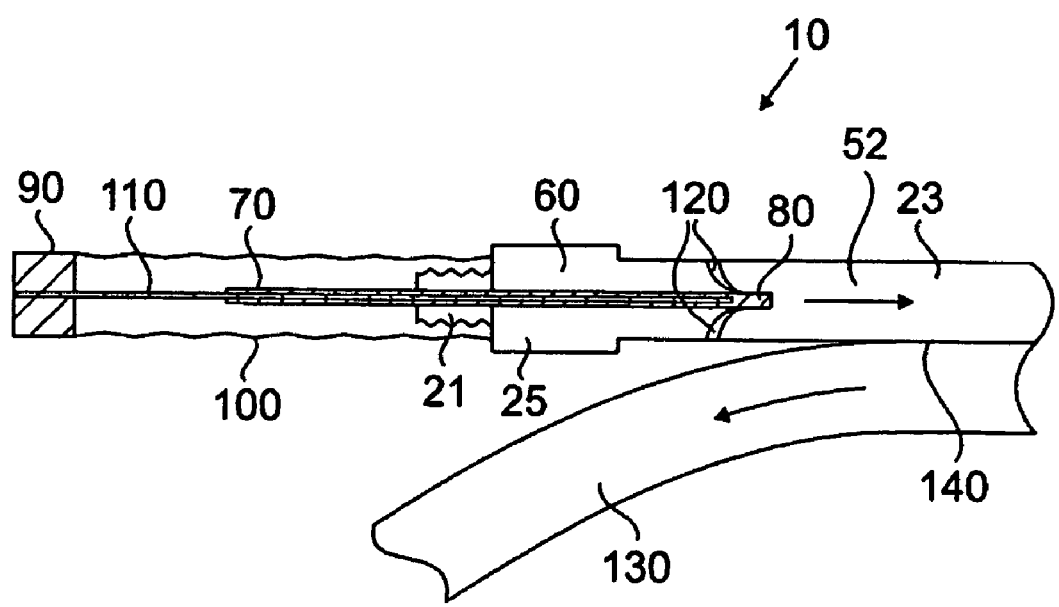
FIG. 6 shows a cross-sectional view of another embodiment of the present invention in which the tip of the rod is loaded with a high concentration of an iodine-based substance to provide a quick release of an anti-microbial agent into the lumen of the catheter. The lumen of the catheter is filled with an aqueous solution.

When the catheter 10 is filled with an aqueous solution, it is preferable to have a higher concentration of the anti-microbial agent substance at the first end 80 of the substrate 60 than at the second end 70 of the substrate 60, i.e., the end attached to the connector or cap 90. FIG. 6 shows an embodiment of the present invention in which the lumen 25 is filled with an aqueous solution. In this embodiment, the first end 80 of the rod is loaded with a higher concentration of an anti-microbial agent than the second end 70 of the rod. The higher concentration at the first end 80 provides a quick release of the agent into the lumen 25 of the catheter 10. In this embodiment, the catheter 10 also includes an outlet lumen 130 and a septum 140 between the inlet lumen 52 and the outlet lumen 130. The septum 140 separates the inlet lumen 52 from the outlet lumen 130. The septum 140 is preferably made from the same materials as the outer walls of the inlet lumen 52 and or outlet lumen 130.

The present invention also provides for a method of assembling a medical device having anti-microbial properties. The method comprises obtaining a medical device with a lumen, such as a catheter 10, and a substrate 60 comprising an anti-microbial agent and having a first end 80 and a second end 70 as described above. The method can also include attaching a connector or cap 90 to the second end 70 of the substrate 60 to facilitate insertion of the substrate 60 into the lumen 25. Furthermore, the method comprises connecting a collapsible cover 100 to the substrate 60 to protect the substrate 60 during insertion into the lumen 25. The first end 80 of the substrate 60 is inserted into the lumen 25 such that the first end 80 is positioned closer to the distal portion 23 of the lumen 25 than the second end 70. The substrate 60 may be inserted into the lumen 25 of the medical device during manufacture or after insertion of the medical device into the body.

The method may further comprise attaching a guidewire 110 to the cap 90, wherein the guidewire 110 contacts the substrate 60 prior to insertion of the substrate 60 into the lumen 25. The guidewire 110 facilitates insertion of the substrate 60 and also provides strength to the substrate 60 during insertion. The guidewire 110 may be removed after insertion of the substrate 60 into the catheter 10. The cap 90 may also be removed after insertion of the substrate 60 into the catheter 10.

In addition, a one-way valve 120 may be included in the lumen 25, wherein the valve 120 is located in the distal portion 23 of the lumen 25 such that at least a portion of the first end 80 of the substrate 60 passes through the valve 120 as the substrate 60 is inserted and positioned in the lumen 25.

The method may also include filling the lumen 25 with an aqueous solution and exposing the substrate 60 to the aqueous solution.

In use, the medical device is introduced into a body lumen in a manner known to the skilled artisan. The medical device can be inserted into the body of a patient so that it contacts any surface of a body lumen. Such body lumen include blood vessels, urinary tract, coronary vasculature, esophagus, trachea, colon, and biliary tract. The medical device may also be inserted through the skin, nose, eyes, breast duct, or ears. The substrate 60 may be inserted into the lumen of the medical device during manufacture or after the medical device has been placed in the body.

The description contained herein is for purposes of illustration and not for purposes of limitation. Changes and modifications may be made to the embodiments of the description and still be within the scope of the invention.

Furthermore, obvious changes, modifications or variations will occur to those skilled in the art. Also, all references cited above are incorporated herein, in their entirety, for all purposes related to this disclosure.

What is claimed is:

1. A system for providing a medical device with anti-microbial properties comprising:
a medical device, having a portion for insertion into the body of a patient, wherein the medical device comprises a lumen having a distal portion and a proximal portion;
a solid rod substrate formed from a polymer material containing an anti-microbial agent, wherein the solid rod substrate has a first end and a second end and wherein the solid rod substrate is capable of being inserted into the lumen in a manner such that the first end of the solid rod substrate is closer to the distal portion of the lumen than the second end of the solid rod substrate; and
a collapsible cover for protecting the solid rod substrate from contamination during insertion of the solid rod substrate into the lumen wherein the cover is connected to the solid rod substrate wherein the cover substantially surrounds the solid rod substrate before the solid rod substrate is inserted into the lumen and extends at least the length of the solid rod substrate and the cover collapses as the solid rod substrate is inserted into the lumen, wherein the solid rod substrate is capable of imparting anti-microbial properties to the lumen of the medical device.

2. A The system of claim 1, further comprising a connector attached to the second end of the solid rod substrate for connecting the solid rod substrate to the cover.

3. The system of claim 2, wherein the connector is a cap.

4. The system of claim 1, wherein the medical device is an in-dwelling catheter.

5. The system of claim 1, wherein the anti-microbial agent comprises an iodine-based substance.

6. The system of claim 1, wherein the anti-microbial agent is only present at the first end of the rod substrate.

7. The system of claim 1, wherein the cover surrounds at least a portion of the solid rod substrate and collapses as the solid rod substrate is inserted into the lumen.

8. The system of claim 1, wherein the cover comprises a polymer selected from the group consisting of polystyrene, polyethylene, polyurethane, polyethylene terephthalate, and polypropylene.

9. The system of claim 1, wherein the solid rod substrate formed from the anti-microbial agent comprises an iodine-polycarbonate material.

10. A system for providing a medical device with anti-microbial properties comprising:
a medical device, having a portion for insertion into the body of a patient, wherein the medical device comprises a lumen having a distal portion and a proximal portion;
a solid rod substrate formed from a polymer material containing an anti-microbial agent comprising an iodine-based substance, wherein the solid rod substrate has a first end and a second end and wherein the solid rod substrate is capable of being inserted into the lumen in a manner such that the first end of the solid rod substrate is closer to the distal portion of the lumen than the second end of the solid rod substrate, wherein the solid rod substrate is capable of imparting anti-microbial properties to the lumen of the medical device; and
a collapsible cover for protecting the solid rod substrate from contamination during insertion of the solid rod substrate into the lumen wherein the cover is connected to the solid rod substrate, wherein the solid rod substrate has a higher concentration of the iodine-based substance at the first end of the solid rod substrate than at the second end of the solid rod substrate.

11. The system of claim 10, wherein the solid rod substrate is formed from the anti-microbial agent.

12. The system of claim 11, wherein the solid rod substrate formed from the anti-microbial agent comprises an iodine-polycarbonate material.

13. A system for providing a catheter with anti-microbial properties comprising a catheter for insertion into the body of a patient having a lumen, wherein the lumen has a proximal portion and a distal portion;
a solid rod formed from a polymer material containing an iodine-based substance, wherein the solid rod has a first end and second end, and wherein the solid rod is capable of being inserted into the lumen in a manner such that the first end of the solid rod is closer to the distal portion of the lumen than the second end of the solid rod, wherein the solid rod is capable of imparting anti-microbial properties to the lumen of the medical device;
a collapsible cover for protecting the solid rod from contamination during insertion of the solid rod into the lumen; and
a cap attached to the second end of the solid rod for connecting the solid rod to the cover.

14. The system of claim 13, wherein the cover surrounds at least a portion of the rod and collapses as the rod is inserted into the lumen.

15. The system of claim 13, wherein the cover comprises a polymer selected from the group consisting of polystyrene, polyethylene, and polyurethane.

16. A catheter having anti-microbial properties provided by the system of claim 13.

17. The system of claim 13, wherein the iodine-based substance comprises an iodine-polycarbonate material.

* * * * *

UNITED STATES PATENT AND TRADEMARK OFFICE
CERTIFICATE OF CORRECTION

PATENT NO. : 7,195,615 B2  Page 1 of 1
APPLICATION NO. : 10/438063
DATED : March 27, 2007
INVENTOR(S) : Sharon Tan It is certified that error appears in the above-identified patent and that said Letters Patent is hereby corrected as shown below:

Title Page item 57
Abstract, first line, after "providing", insert -- a --.
Specification, Col. 1, line 10, after "properties", insert --,-- and delete "and".
Specification, Col. 1, line 45, after "microbial" chance "grown" to -- growth --.
Specification, Col. 2, line 11, after "Such" insert -- an --.
Specification, Col. 3, line 38, before "method", insert -- a --.
Specification, Col. 8, line 57, after "lumen" (second occurrence), change "include" to -- includes --.
Specification, Col. 9, line 23, after "substrate," insert -- , --.
Specification, Col, 9, line 28, after "lumen,", insert -- and --.
Specification, Col. 9, line 40, before "rod", insert -- solid --.
Specification, Col. 10, line 45, before "rod" (first occurrence), insert -- solid--.
Specification, Col. 10, line 45, before "rod" (second occurrence), insert -- solid--.

Signed and Sealed this

Eighteenth Day of December, 2007

JON W. DUDAS
*Director of the United States Patent and Trademark Office*